(12) United States Patent
Fowler et al.

(10) Patent No.: US 8,920,342 B2
(45) Date of Patent: Dec. 30, 2014

(54) SINGLE-USE LANCET SENSOR ASSEMBLY AND METER

(71) Applicant: Nova Biomedical Corporation, Waltham, MA (US)

(72) Inventors: James Fowler, Brewster, MA (US); Robert Daggett, Chelmsford, MA (US)

(73) Assignee: Nova Biomedical Corporation, Waltham, MA (US)

( * ) Notice: Subject to any disclaimer, the term of this patent is extended or adjusted under 35 U.S.C. 154(b) by 63 days.

(21) Appl. No.: 13/890,451

(22) Filed: May 9, 2013

(65) Prior Publication Data

US 2013/0253373 A1    Sep. 26, 2013

Related U.S. Application Data

(62) Division of application No. 12/187,416, filed on Aug. 7, 2008, now Pat. No. 8,449,480.

(51) Int. Cl.
*A61B 5/00* (2006.01)
*A61B 5/15* (2006.01)
*A61B 5/145* (2006.01)
*A61B 5/151* (2006.01)
*A61B 5/157* (2006.01)
*A61B 19/00* (2006.01)

(52) U.S. Cl.
CPC ......... *A61B 5/150916* (2013.01); *A61B 5/1411* (2013.01); *A61B 5/14532* (2013.01); *A61B 5/150022* (2013.01); *A61B 5/15019* (2013.01); *A61B 5/150725* (2013.01); *A61B 5/15113* (2013.01); *A61B 5/15117* (2013.01); *A61B 5/1513* (2013.01); *A61B 5/1519* (2013.01); *A61B 5/157* (2013.01); *A61B 5/15148* (2013.01); *A61B 5/150267* (2013.01); *A61B 5/150297* (2013.01); *A61B 5/150358* (2013.01); *A61B 5/150412* (2013.01); *A61B 5/150564* (2013.01); *A61B 5/15194* (2013.01); *A61B 2019/442* (2013.01); *A61B 2562/0295* (2013.01)
USPC ....................................................... 600/583

(58) Field of Classification Search
CPC ........... A61B 5/150916; A61B 5/1411; A61B 5/14532; A61B 5/150022; A61B 5/15019; A61B 5/150725; A61B 5/15113; A61B 5/15117; A61B 5/1513; A61B 5/1519; A61B 5/157; A61B 5/15148
USPC ........................... 600/583; 606/181–183, 167
See application file for complete search history.

(56) References Cited

U.S. PATENT DOCUMENTS

| | | | | |
|---|---|---|---|---|
| 5,423,847 | A * | 6/1995 | Strong et al. | 606/182 |
| 6,168,606 | B1 * | 1/2001 | Levin et al. | 606/181 |
| 6,514,270 | B1 * | 2/2003 | Schraga | 606/182 |
| 2006/0020228 | A1 * | 1/2006 | Fowler et al. | 600/583 |
| 2007/0149897 | A1 * | 6/2007 | Ghesquiere et al. | 600/583 |

* cited by examiner

*Primary Examiner* — Brian Szmal
(74) *Attorney, Agent, or Firm* — Robert R. Deleault, Esq.; Mesmer & Deleault, PLLC

(57) ABSTRACT

A single-use lancet cartridge for inserting into a multi-use lancet driver assembly of a meter housing includes an elongated lancet housing with an open end, a lancet within the lancet housing and movable between a retracted and resting orientation to a piercing orientation through the open end, and a re-use prevention component that is a rotated drive wing incorporated within the lancet cartridge and oriented to cooperatively engage with a driver piston of the multi-use lancet driver assembly only one time thereby preventing the lancet from being moved into a piercing orientation a second time.

12 Claims, 12 Drawing Sheets

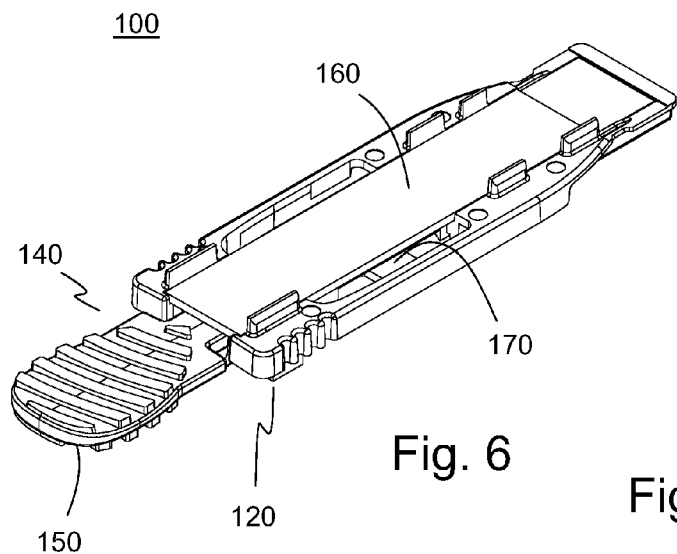
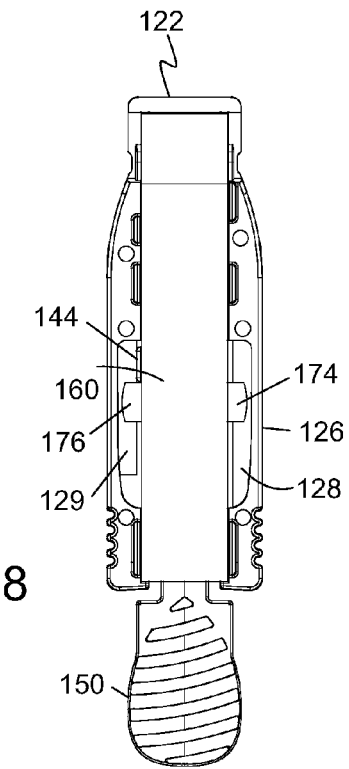
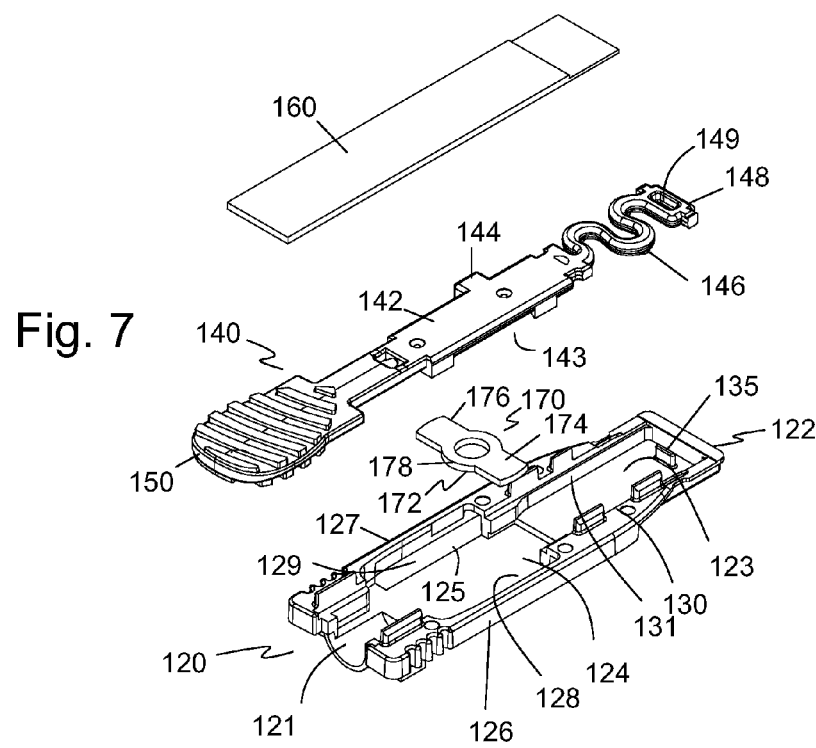

SINGLE-USE LANCET SENSOR ASSEMBLY AND METER

This application is a Divisional application of Ser. No. 12/187,416, filed on Aug. 7, 2008.

BACKGROUND OF THE INVENTION

1. Field of the Invention

The present invention relates generally to a lancet device. Particularly, the present invention relates to a single use lancet device that prevents re-use of the lancet.

2. Description of the Prior Art

Lancets are well-known devices commonly used in the medical field to make small punctures in a patient's skin in order to obtain samples of blood. They are utilized in hospitals, other medical facilities and by private individuals such as diabetics for testing droplets of blood for various analytes. Typically, lancets are used only once in order to reduce the risk of HIV, hepatitis and other bloodborne diseases. The needle of these devices is driven into the patient's skin by a small spring that is cocked by a technician or user prior to use. The needle is covered with a protective, safety cap that is removed before use. The safety cap keeps the end of the lancet sterile and is typically used as a kind of pushrod for arming the device. After arming the device, the safety cap is removed exposing the needle and the lancet is ready for use.

There are a variety of lancet devices that are available for utilization by patients and/or practitioners in a variety of different circumstances. One variety is configured for multiple and/or repeated uses. This variety typically includes a lancet injector that projects a lancet toward the skin of a patient that is pushed by the user. More commonly, the lancet device effectively encases and fires the lancet into the patient's skin in order to puncture in an accurate, standardized and consistent manner. The lancet injector may also be provided with an adaptor cap to control and adjust the depth of penetration of the needle of the lancet.

Another variety is configured for single use where the entire device is discarded after use. Typically, these devices include a housing that contains and directs or drives a piercing tip into the patient's skin and then is discarded along with the used lancet. Such devices are effective for achieving the piercing of the skin required for effective operation. These single-use, disposable devices, however, typically do not incorporate a large number of safety features to ensure safe use and disposal of the device. A major disadvantage of such devices is that they can be inadvertently re-used. The configuration of these devices is such that a user can re-cock the device and allow for subsequent and inappropriate use of a contaminated lancet.

There have been some devices developed that affirmatively prevent re-use of a single use lancet. U.S. Pat. No. 5,423,847 (1995, Strong et al.) discloses a safe lancet injector. The safe lancet injector for use with a lancet and an isolating platform to obtain blood samples for diagnostic purposes. The lancet injector uses two elastomeric bands to push the lancet forward and to rapidly withdraw the needle from the skin. It further includes an interlocking mechanism that completely precludes a lancet from being used more than once, which causes the used lancet to be ejected before cocking/arming the lancet injector can be performed.

U.S. Pat. No. 6,168,606 (2001, Levin et al.) discloses a single-use, spring-driven lancet device. The device is pre-cocked during assembly so that the user needs only to remove the safety cap prior to use. A thin plastic fiber connection between the pull-tab and the needle safety cap prevents any compressive force from being applied to the drive spring, which prevents recocking/re-arming of the device.

U.S. Pat. No. 6,514,270 (2003, Schraga) discloses a single use lancet device having a housing, a lancet with a piercing tip movably disposed in the housing and structured to move between a cocked orientation and a piercing orientation, and a driving assembly structured to move the lancet into the piercing orientation. A retention member and an engagement hub are provided and structured to cooperatively engage with one another when the lancet is disposed into the cocked orientation until released by an actuation assembly. The actuation assembly is structured to move between an actuated and an un-actuated orientation. Movement of the actuation member into the actuated orientation releases the retention member and the engagement hub from their cooperative engagement with one another resulting in the movement of the lancet into the piercing orientation. A restrictor assembly prevents the actuation assembly from moving out of the actuated orientation and prevents re-firing of the lancet using the actuation assembly.

These devices, however, are only lancet devices and must be used with separate test strips for making an analyte determination on the sample of blood produced by the lancet device.

There has also been developed integrated lancet and sensor devices that combine the lancet and test strip into a single package. These integrated devices are typically used with a lancet injector where the integrated lancet and test strip is removed from the lancet injector and connected to a meter after acquisition by the test strip of the blood sample produced by the lancet, or used with a meter with built-in lancet injector.

One such integrated device is disclosed in U.S. Patent Application Publication 2007/0149897 by Ghesquiere et al. The device is an integrated lancet and testing striplet for measuring a body analyte level in a health care regimen that includes a lancet needle and an analyte sensor coupled together. A lancet body includes a sensor receiving end and a lancet end. The lancet needle is coupled with and protruding from the lancet end. The sensor is coupled to the sensor receiving end of the lancet body. The integrated device is positioned within a rotating cradle and, during the assay or after completion of the assay, the cradle is rotated by mechanical transmission to position the lancet for re-attaching the protective cover to the used lancet of the lancet-test strip combination.

U.S. Patent Application Publication 2006/0020228 (2006, Fowler et al.) discloses an integrated lancet and test strip. The assembly includes a lancet disposed within a lancet enclosure where the lancet moves between a retracted position and an extended position out of a needle end of the lancet enclosure, and an elongated test strip having a sample receiving end disposed at the needle end of the lancet enclosure. After piercing the skin, the lancet is retracted into the lancet enclosure so that it is not exposed to prevent accidental piercing.

A major disadvantage of these integrated lancet and test strip devices is the lack of a safety mechanism to prevent re-firing/re-use of a used integrated device. Prior art devices can be inadvertently re-fired by simply re-cocking the firing mechanism, which can lead to inadvertent and accidental skin punctures with a used lancet.

Therefore, what is needed is lancet device that is a single use lancet with a safety mechanism to prevent re-use. What is also needed is an integrated lancet and test strip device where the lancet portion cannot be re-fired/re-used.

SUMMARY OF THE INVENTION

It is an object of the present invention to provide a lancet device that can only be used one time. It is another object of the present invention to provide an integrated lancet sensor system that cannot be accidentally re-used.

The present invention achieves these and other objectives by providing a safety lancet system that includes at least a single-use lancet assembly with a re-use prevention component and a separate multi-use lancet driver assembly. The single-use lancet assembly includes a re-use prevention component. The single-use lancet assembly with the re-use prevention component is operably combined with the multi-use lancet driver assembly where the re-use prevention component of the single-use lancet assembly is configured to prevent the lancet from extending out of the lancet assembly and into a piercing orientation after an initial use. Particularly, the re-use prevention component interacts with a lancet driver piston of the lancet driver assembly. The lancet driver assembly is reusable while the lancet assembly is a one-time use device. The lancet driver assembly is configured for engaging a lancet of the lancet assembly and, when activated, to extend the lancet into a piercing orientation before disengaging the lancet. The multi-use lancet driver assembly further includes an activating trigger that is cooperatively connected to the driver piston when the driver piston is in a cocked or armed orientation.

In one embodiment of the present invention, the single-use lancet assembly of the safety lancet system includes a cocking tab that engages the lancet driver piston of the lancet driver assembly. The cocking tab arms the lancet driver piston when the single-use lancet assembly is operably combined with the multi-use lancet driver assembly. The cocking tab is removed from the single-use lancet assembly after arming the lancet driver piston. Optionally, the cocking tab is integrally connected to a needle safety cap that maintains the needle of the lancet in a sterile condition until use. When the needle safety cap is removed from the needle of the single-use lancet assembly, the cocking tab is also removed simultaneously. It is the cocking tab of the single-use lancet assembly that arms the lancet driver assembly. Once the cocking tab is removed, it cannot be re-assembled into the single-use lancet assembly. Without the cocking tab, any re-combining of the used lancet assembly with the multi-use lancet driver assembly will fail to arm the driver piston since the piston interface surface of the cocking tab is missing. Consequently, the single-use lancet assembly cannot be re-used and any inadvertent attempt to re-use a previously used lancet assembly is prevented.

In another embodiment of the present invention, the single-use lancet assembly of the safety lancet system includes a rotating drive wing that is engaged by the lancet driver piston of the lancet driver assembly upon activation after the single-use lancet assembly is operably combined with the multi-use lancet driver assembly. The lancet driver piston also includes a drive wing pawl that engages the rotating drive wing upon the return of the lancet driver piston after the lancet has achieved its piercing orientation. The drive wing pawl rotates the drive wing into a non-engageable orientation during the return of the lancet driver piston to its resting orientation.

In another embodiment of the present invention the single-use lancet assembly includes an anti-rotation wing stop that prevents the rotating drive wing from rotating into a non-engageable orientation before the initial use of the lancet assembly.

In still another embodiment of the present invention, the lancet driver piston of the multi-use lancet driver assembly includes a deflectable drive wing pawl. The drive wing pawl has a wing rotating surface that is engageable with the rotatable drive wing after the driver piston has moved the lancet into a piercing orientation. The wing rotating surface contacts the rotatable drive wing and rotates the rotatable drive wing into a non-engageable orientation during the driver piston's return to the resting orientation.

In another embodiment of the present invention, the multi-use lancet driver assembly is housed within a system enclosure and includes a lancet cartridge lock. The lancet cartridge lock has an elongated and biasing member with a locking tab extending laterally from the biasing member. The locking tab is situated for cooperative and biasing engagement with a notch in the bottom of the single-use lancet cartridge, preferably along the central longitudinal axis of the lancet cartridge, when a lancet cartridge is inserted into a lancet cartridge receiving port of the system enclosure.

In another embodiment of the present invention, the multi-use lancet driver assembly includes an ejector member. The ejector member has an ejector body with a tab engaging surface, a lancet cartridge ejecting surface and a discharge button laterally and integrally connected to the ejector body. The discharge button is disposed outside of the system enclosure and slidably moves to eject the lancet cartridge. The tab engaging surface is positioned to engage the locking tab before the lancet cartridge ejecting surface engages the lancet cartridge when the discharge button is actuated.

In yet another embodiment of the present invention, the multi-use lancet driver assembly includes a depth setting gauge that has a driver piston engaging surface, which is non-planar, situated within the system enclosure for cooperative engagement with a portion of the driver piston of the multi-use lancet driver assembly. An outer surface portion of the depth setting gauge extends outside of the system enclosure to allow selecting a predefined depth penetration of the lancet into the specimen.

In still another embodiment of the present invention, the multi-use lancet driver assembly includes an arming member. The arming member has an arming member body and a cocking button laterally and integrally connected to the arming member body. The cocking button is disposed outside of the system enclosure to slidably move the drive piston into a cocked orientation.

In another embodiment of the present invention, the multi-use lancet driver assembly includes an electronic measuring module disposed within the system enclosure for measuring the concentration of an analyte when the lancet cartridge incorporates a single-use sensor strip integrally connected to the lancet cartridge. The electronic measuring module has a sensor strip interface for electronically coupling to the sensor strip.

In a further embodiment of the present invention, the multi-use lancet driver assembly includes a scanner module within the system enclosure that is electronically coupled to the electronic measuring module. The scanner module scans a unique patient bar code that allows the analyte measurement to be associated with the patient possessing the patient bar code.

BRIEF DESCRIPTION OF THE DRAWINGS

FIG. 6 is a perspective view of another embodiment of the single-use lancet and sensor assembly of the present invention.

FIG. 7 an exploded, perspective view of the embodiment in FIG. 6 showing the lancet housing, the lancet, the re-use prevention component that is a rotating wing, and the sensor strip.

FIG. 8 is a top view of the embodiment in FIG. 6.

DETAILED DESCRIPTION OF THE PREFERRED EMBODIMENT

Figure 1:
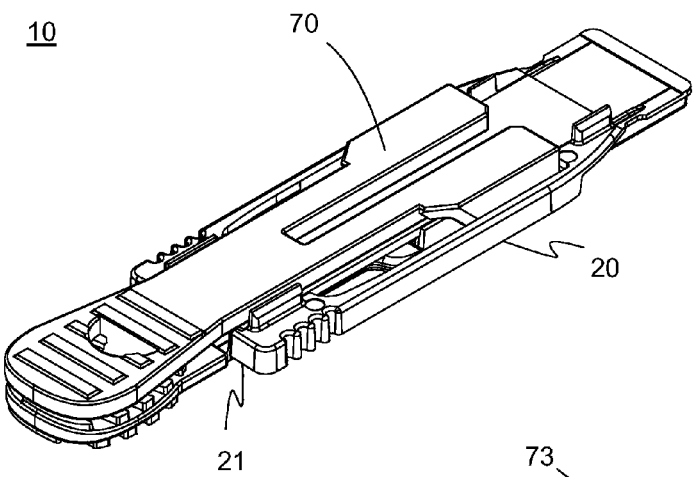
FIG. 1 is perspective view of one embodiment of the safety lancet and sensor assembly of the present invention.
Figure 2:
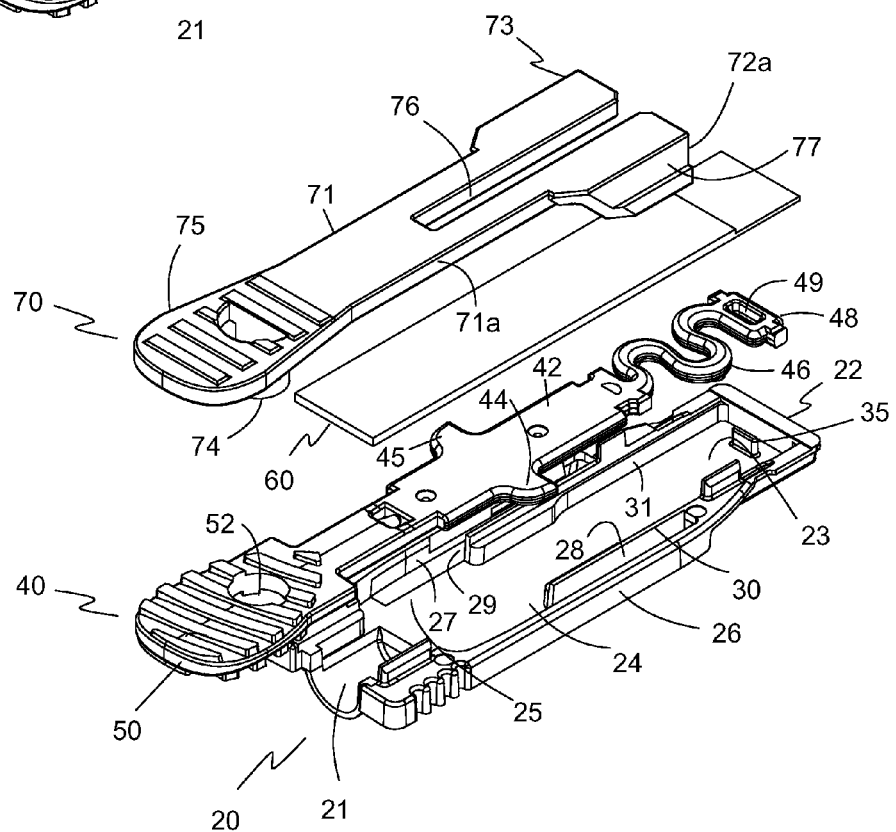
FIG. 2 is an exploded, perspective view of the embodiment in FIG. 1 showing the lancet housing, the lancet, the sensor strip, and the re-use prevention component.

The preferred embodiment(s) of the present invention is illustrated in FIGS. 1-16. FIG. 1 illustrates one embodiment of the single-use lancet cartridge 10 of the present invention for use with a multi-use lancet driver assembly and meter. Lancet cartridge 10 incorporates a re-use prevention component 70 that cooperates and engages with a driver piston similar to the one shown in FIGS. 10-12. Re-use prevention component 70 is removably coupled to a lancet housing 20 as the top component in the lancet cartridge 10 with a portion extending beyond lancet housing end 21. FIG. 2 is an expanded view of lancet cartridge 10 showing the various components that are assembled to form lancet cartridge 10. Lancet cartridge 10 includes a lancet housing 20, a lancet 40, a sensor test strip 60, and re-use prevention component 70.

Lancet housing 20 includes a housing recess 23 that is configured to receive and contain lancet 40 when lancet cartridge 10 is in a static state. Lancet housing 20 has a housing open end 21 through which lancet 40 protrudes and retracts during use and a housing closed end 22. Lancet 40 has a first drive wing 44 and an optional second drive wing 45 that extend out the sides of lancet housing 20. Lancet housing 20 may be made of metal or a plastic material such as, for example, polyvinyl chloride, polycarbonate, polysulfone, nylon, polyurethane, cellulose nitrate, cellulose propionate, cellulose acetate, cellulose acetate butyrate, polyester, acrylic, and polystyrene.

Lancet housing 20 includes a housing recess 23, a first side opening 24, a second side opening 25 and an optional first and second wing guards 26, 27. When optional first and second wing guards 26, 27 are incorporated into lancet housing 20, there are formed driver piston channels 28, 29 between first wing guards 26, 27 and the sides 30, 31 of lancet housing 20, respectively. First and second side openings 24, 25 are sufficiently elongated to allow the lancet 40 to move between a retracted and resting orientation and exposed piercing orientation.

Lancet 40 includes a lancet body 42 having first and second drive wings 44, 45, a biasing member 46, a lancet needle 48 (shown in FIGS. 9 and 12), and an optional needle safety cap 50. Optional needle safety cap 50 includes a tab capturing opening 52. Biasing member 46 is directly connected to lancet body 42 on one end and includes an anchoring component 48 at the opposite end. Anchoring component 48 preferably includes a slot 49 that receives a retaining flange 35 of lancet housing 20. Anchoring component 48 fixes one end of lancet 40 so that biasing member 46 functions as intended, which is to pull the lancet body 42 and lancet needle 48 back into a retracted orientation within lancet housing 20 after having been moved to exposed piercing orientation by the driver piston.

Sensor test strip 60 is a disposable sensor strip capable of measuring the concentration of a predefined analyte in a liquid sample. An example of such a sensor test strip is a disposable glucose test strip for measuring blood glucose. However, disposable strips designed to measure other analytes may also be incorporated into lancet cartridge 10.

Re-use prevention component 70 in this embodiment is a removable, elongated, piston cocking tab 71 (shown in FIG. 2) having at least one driver piston engageable surface 72 located at a first tab end 73 and a needle cap interlocking mechanism 74 at or near a second tab end 75. Piston cocking tab 71 may optionally include an alignment notch 76, which may cooperate with an alignment tab within the meter housing to which the lancet cartridge 10 is coupled.

Figure 3:
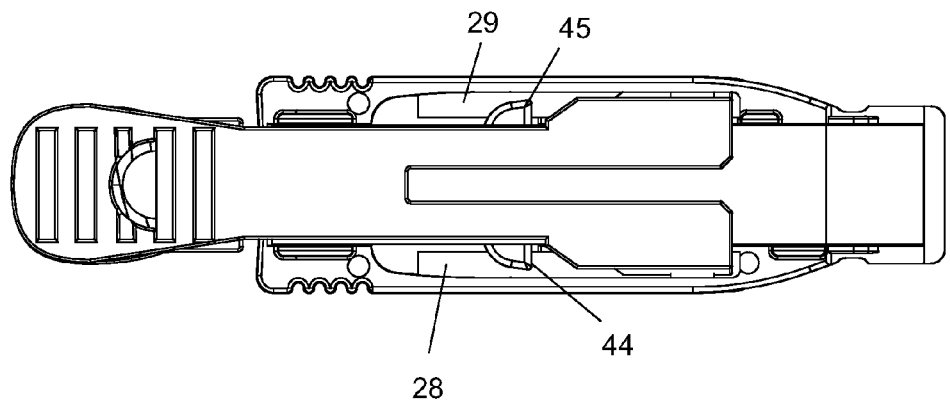
FIG. 3 is a top view of the embodiment in FIG. 1.

Turning now to FIG. 3, there is illustrated a top view of lancet cartridge 10 of the embodiment of FIG. 1. As is more clearly shown, first and second drive wings 44, 45 extend outwardly and perpendicularly from housing sides 30, 31 (shown in FIG. 2) into drive channels 28, 29. It is important to note that lancet cartridge 10 is unusable without a meter housing that incorporates a lancet driver mechanism to drive lancet 40 (shown in FIG. 2) from a retracted orientation to exposed piercing orientation.

Figure 4:
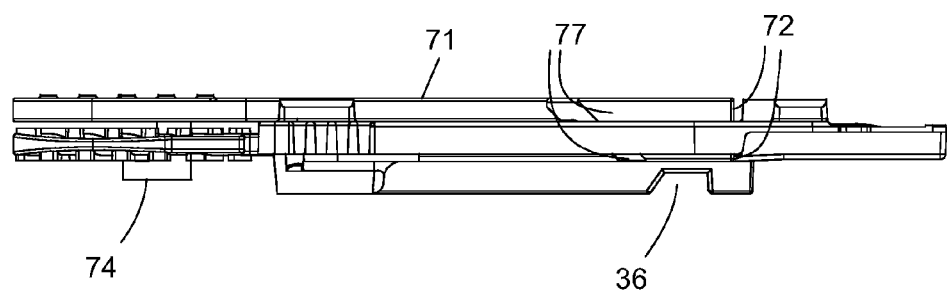
FIG. 4 is a side view of the embodiment in FIG. 1 showing the housing retention notch and the re-use prevention component connected to the lancet.

FIG. 4 shows a side view of lancet cartridge 10. Referring back to FIG. 2, piston cocking tab 71 includes a piston flange 77 that extends laterally and downwardly from a first side edge 71a into piston channel 28 behind first drive wing 44 and closer to housing closed end 22. Piston flange 77 includes driver piston engageable surface 72. Optionally, piston cocking tab 71 may include a second piston flange 78 that extends laterally and downwardly from a second side edge 71b shown in FIG. 5. Needle cap interlocking mechanism 74 extends through tab capture opening 52 of needle safety cap 50 and interlocks piston cocking tab 71 with needle safety cap 50. When lancet cartridge 10 is inserted into a meter housing having an appropriate lancet driver mechanism, the driver piston engageable surface 72 engages the lancet driver piston and pushes the lancet driver piston into an armed position. When needle safety cap 50 is removed from lancet cartridge 10 after lancet cartridge 10 is inserted into the meter housing and the piston cocking tab 71 has armed the lancet driver piston within the meter housing, piston cocking tab 71 is also simultaneously removed from lancet cartridge 10. The removal of piston cocking tab 71 from lancet cartridge 10 effectively removes the cocking mechanism that arms the lancet driver piston situated in the meter housing.

After lancet cartridge 10 is used to lance a specimen, lancet cartridge 10 no longer has the necessary cocking tab 71 to re-arm the lancet driver piston. If the used lancet cartridge 10 is removed from the meter and then reinserted, there is no piston engageable surface 72 to engage the lancet driver piston and to drive the piston into the armed position. Where the lancet driver piston cannot be re-armed with a previously used lancet cartridge 10, it is not possible to reuse a previously used lancet cartridge 10 for lancing the same or another specimen to obtain a test sample. Thus, the lancet cartridge 10 is truly a single-use lancet cartridge.

Another feature that is more clearly shown in FIG. 4 is the lancet cartridge retainer notch 36. Cartridge retainer notch 36 cooperates with a locking mechanism within the meter housing to retain lancet cartridge 10 coupled with the meter housing until it is desired to remove lancet cartridge 10 from the meter housing.

Figure 5:
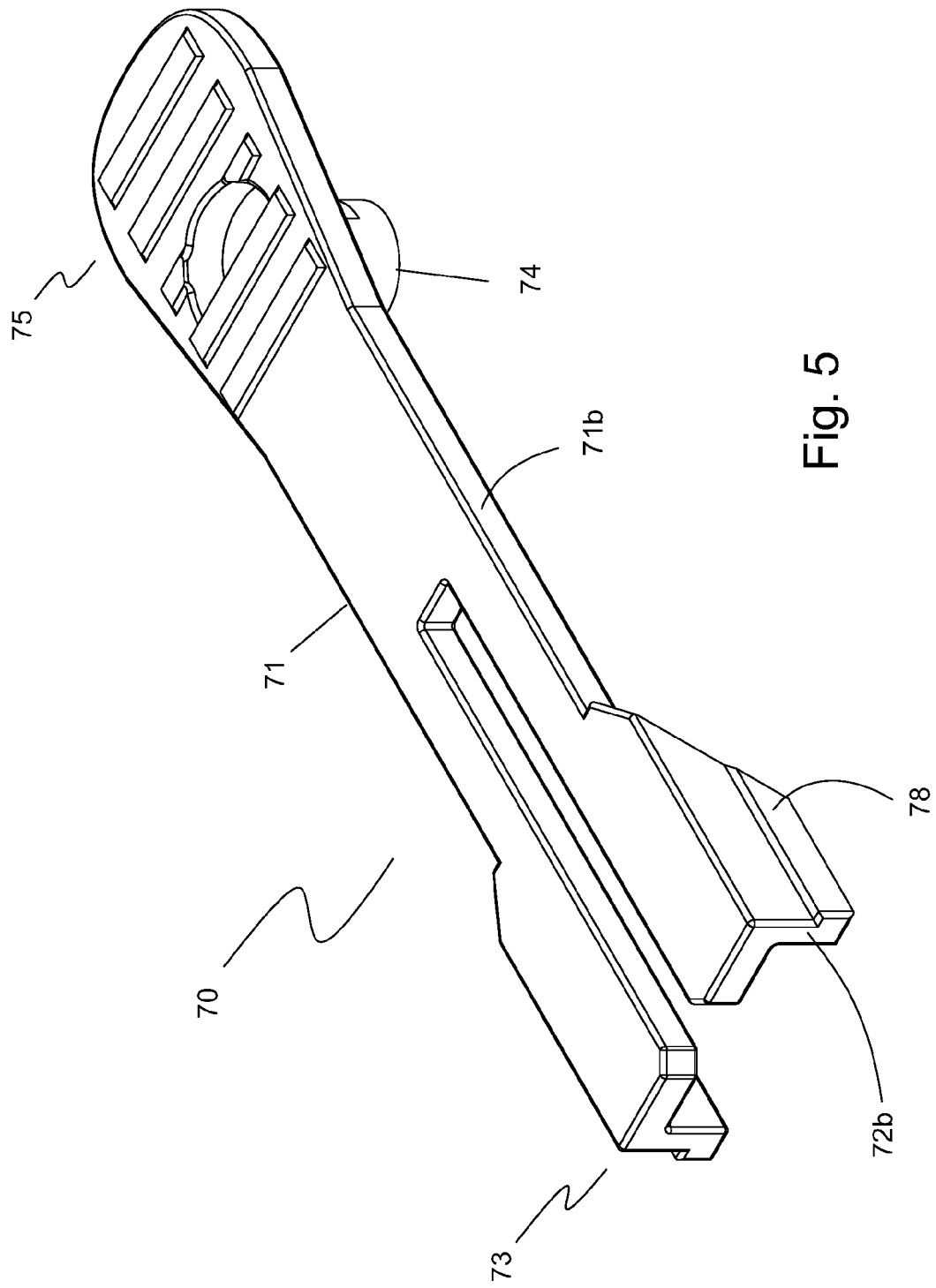
FIG. 5 is an enlarged, perspective view of the re-use prevention component in FIGS. 1 and 2.

Turning now to FIG. 5, there is illustrated an enlarged perspective view of the re-use prevention component 70. As previously disclosed, the cocking tab 71 includes the needle cap interlocking mechanism 74, which is a flange that is inserted into the tab capture opening 52 of needle safety cap 50, adjacent the second tab end 75, and the piston flange 77 that extends laterally and downwardly from cocking tab 71 at the first tab end 73 with the piston engageable surface 72.

FIG. 6 illustrates another embodiment of single-use lancet cartridge 10 for use with a multi-use lancet driver assembly and meter. In this embodiment, lancet cartridge 100 incorporates a re-use prevention component 170 that cooperates and engages with a driver piston shown in FIGS. 10-12. Unlike the previously disclosed embodiment, only the needle safety cap 150 extends out of the open end 121 of lancet housing 120. FIG. 7 is an expanded view of lancet cartridge 100 showing the various components that are assembled to form lancet cartridge 100. Lancet cartridge 100 includes a lancet housing 120, a lancet 140, a sensor test strip 160, and re-use prevention component 170. Like in the previously disclosed embodiment, lancet housing 120 includes a housing recess 123 that is configured to receive and contain lancet 140 when lancet cartridge 100 is in a static state. Lancet housing 120 has a housing open end 121 through which lancet 140 protrudes and retracts during use and a housing closed end 122.

Lancet housing 120 also includes a first side opening 124, an optional second side opening 125 and an optional first and second wing guards 126, 127. When optional first and second wing guards 126, 127 are incorporated into lancet housing 120, there are formed driver piston channels 128, 129 between first wing guards 126, 127 and the sides 130, 131 of lancet housing 120, respectively. First and second side openings 124, 125 are sufficiently elongated to allow the lancet 140 to move between a retracted and resting orientation and a piercing orientation.

Lancet 140 includes a lancet body 142 having a rotatable drive wing mount 143 (not shown) on one side of lancet body 142, a rotatable drive wing stop 144, a biasing member 146, a lancet needle 148 (shown in FIGS. 9 and 12), and an optional needle safety cap 150. Biasing member 146 is directly connected to lancet body 142 on one end and includes an anchoring component 148 at the opposite end. Anchoring component 148 preferably includes a slot 149 that receives a retaining flange 135 of lancet housing 120. Anchoring component 148 fixes one end of lancet 140 so that biasing member 146 functions as intended, which is to pull the lancet body 142 and lancet needle 148 back into a retracted and resting orientation within lancet housing 120 after having been moved to a piercing orientation by the driver piston.

Sensor strip 160 incorporated in lancet cartridge 100 is the same or similar to sensor strip 60 previously disclosed.

Re-use prevention component 170 in this embodiment is a rotatable drive wing 172 that is rotatably mounted onto lancet 140 by way of the drive wing mount 143. Rotatable drive wing 172 includes a first drive wing portion 174, a second drive wing portion 176 and a middle drive wing portion 178 that directly connects to first and second drive wing portions 174, 176. Middle drive wing portion 178 is rotatably mounted to rotatable wing mount 143 of lancet body 142. First drive wing portion 174 extends out through a first side opening 124 and second drive wing portion 176 is positioned to be engageable with drive wing stop 144. It should be understood that second drive wing portion 176 may optionally extend sufficiently from middle drive wing portion 178 to also extend out through the optional second side opening 125 of lancet housing 120.

FIG. 8 illustrates a top view of lancet cartridge 100. As more clearly shown, first and second drive wing portions 174, 176 extend outwardly and perpendicularly from housing sides 130, 131 (shown in FIG. 7) and into drive channels 128, 129. As with the prior embodiment, this embodiment of lancet cartridge 100 is also unusable without a meter housing that incorporates a lancet driver mechanism to drive lancet 140 from a retracted orientation to a piercing orientation.

Figure 9:
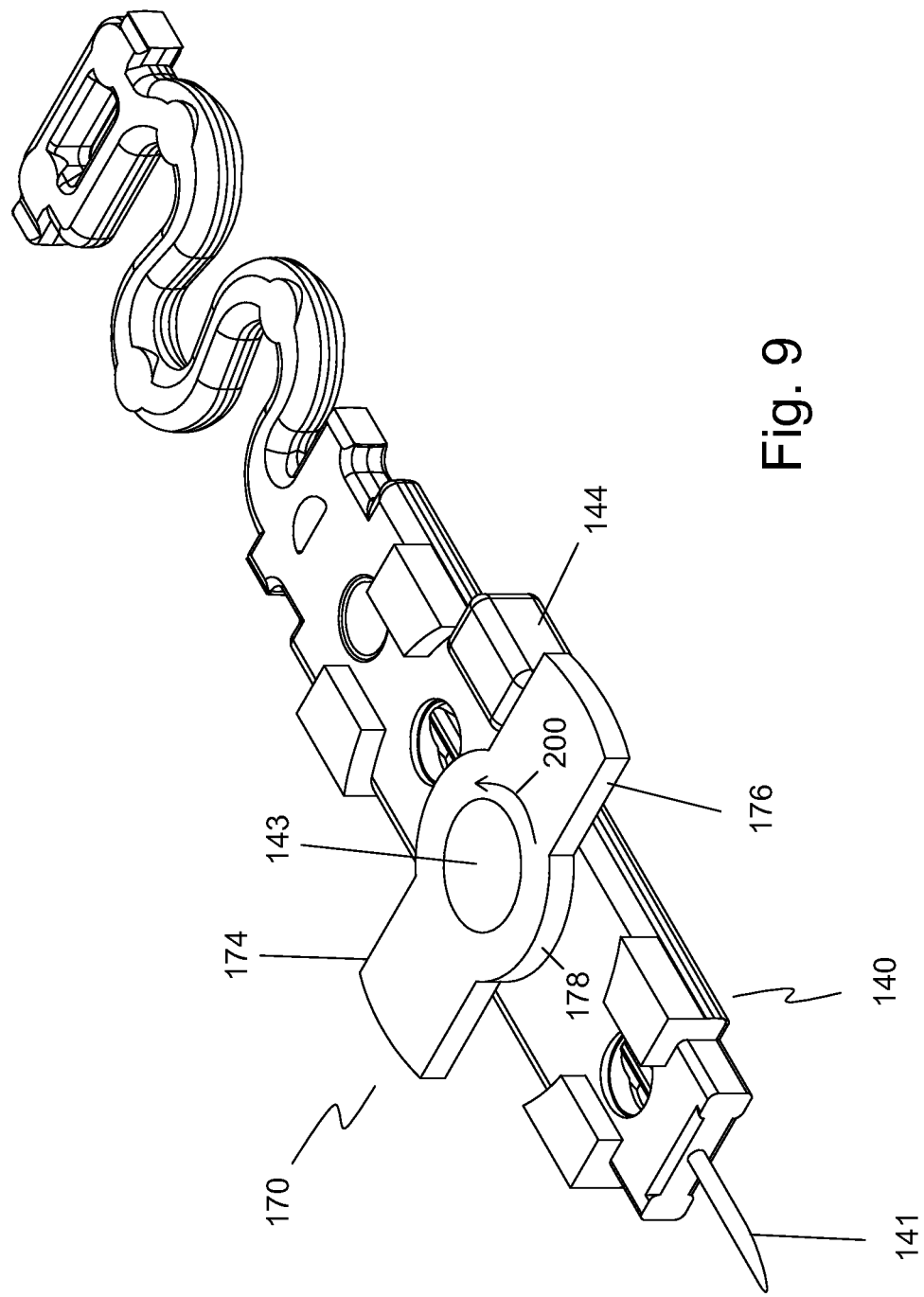
FIG. 9 is an enlarged, bottom, perspective view of the lancet and rotating wing in FIG. 8.

FIG. 9 shows an enlarged, perspective, bottom view of lancet 140 with rotatable drive wing 170 mounted thereon. Rotatable drive wing 170 is rotatably mounted onto rotatable drive wing mount 143 with second wing portion 176 in contact with drive wing stop 144. Drive wing stop 144 prevents rotatable drive wing 170 from rotating in the direction of arrow 200 so that the first and second drive wing portions 174, 176 extend approximately perpendicularly from lancet body 142 in order to present the drive wing portions 174, 176 in proper position for contact from the lancet driver piston when lancet cartridge 100 is inserted into the meter housing.

Figure 10:
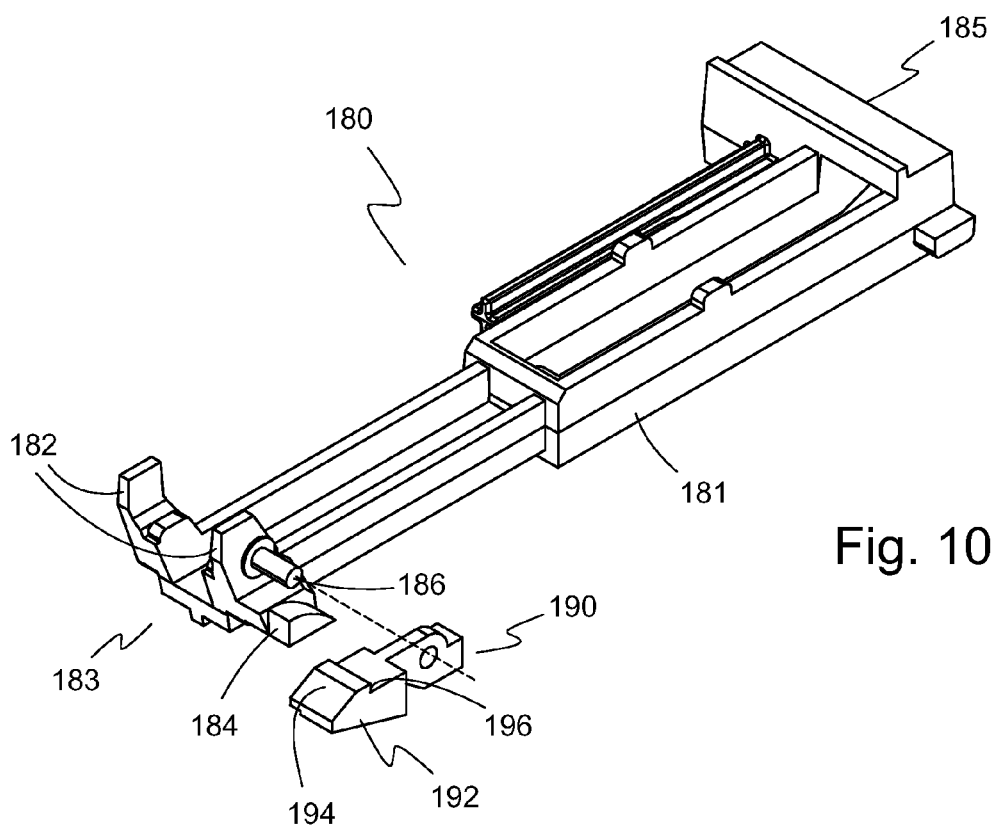
FIG. 10 is an exploded, perspective view of the lancet driver and pawl used for engaging the rotating wing of the lancet.
Figure 11:
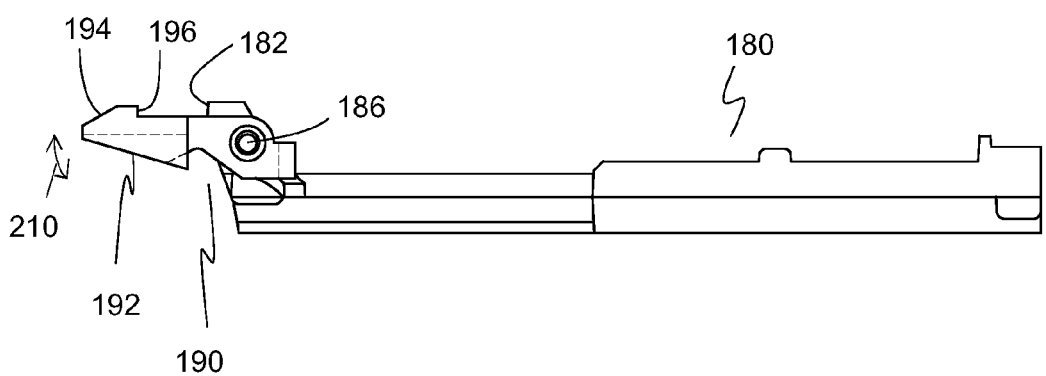
FIG. 11 is a side view of the assembled lancet driver and pawl in FIG. 10.
Figure 12:
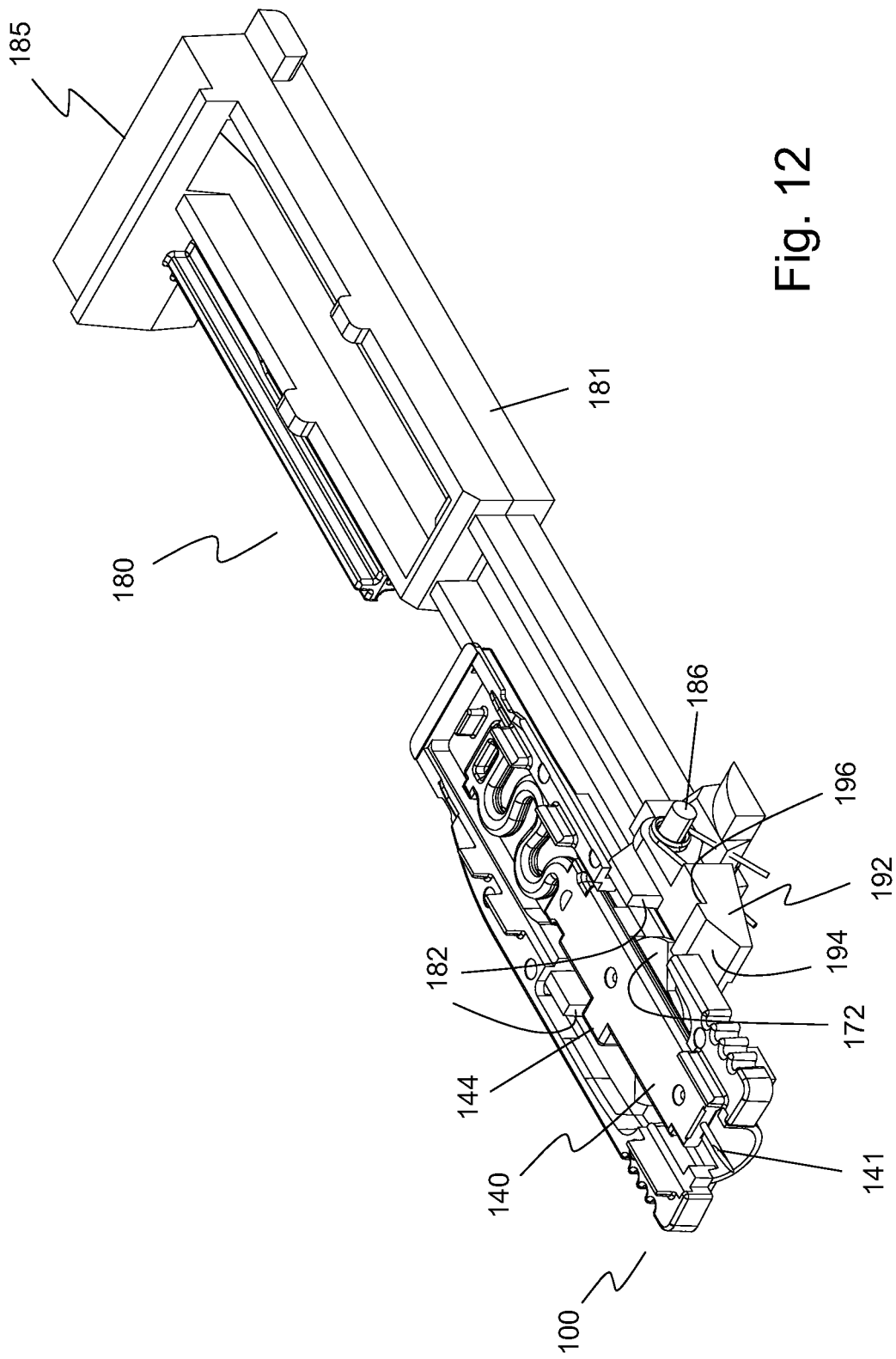
FIG. 12 is a perspective view of the lancet cartridge and lancet driver showing the pawl engaging the rotating wing after driving the lancet to its piercing orientation.

In order for the re-use prevention component 170 in this embodiment to function as desired, lancet driver piston must incorporate a component to interact with rotatable drive wing 170. FIGS. 10 and 11 illustrate one embodiment of a lancet driver piston 180 for use with lancet cartridge 100. Driver piston 180 includes a piston body 181 having ends 183, 185 and a drive wing piston surface 182 at end 183, a trigger release stop 184, a wing pawl 190 and a pawl mount 186. Wing pawl 190 is rotatably mounted on pawl mount 186 with a pawl spring (not shown) to provide a limited range of motion indicated by arrow 210. Pawl 190 includes a wing engageable portion 192 that includes a wing deflector surface 194 and a wing rotating surface 196. Wing engageable portion 192 of pawl 190 extends beyond drive wing piston surface 182 a sufficient distance such that first drive wing portion 174 lies between wing rotating surface 196 and drive wing piston surface 182 when lancet driver piston 180 is fired from an armed position to move the lancet needle and body 141, 142, respectively, from the retracted and resting orientation to the piercing orientation after lancet cartridge 100 is loaded into a meter housing containing lancet driver piston 180. During the firing or activating process, wing deflector surface 194 contacts first wing portion 174. Because wing stop 144 prevents rotatable drive wing 172 from rotating, pawl 190 is deflected below first wing portion 174 and until shortly before drive wing piston surface 182 contacts first wing portion 174. Upon return of driver piston 180 after driving lancet needle 141 to its piercing orientation, wing rotating surface 196 of pawl 190 engages first wing portion 174 and rotates rotatable drive wing 172 to position first drive wing portion 174 within lancet housing 120 so that first drive wing portion 174 no longer extends out of lancet housing 120 and no longer presents a surface upon which drive wing piston surface 182 can engage. Due to the rotation of drive wing 172, re-arming and firing/activating of lancet driver piston 180 fails to drive lancet needle 141 and lancet body 142 into a piercing orientation after the first use. FIG. 12 illustrates wing rotating surface 196 of pawl 190 rotating rotatable drive wing 172 during the return of lancet driver piston 180 after having driven lancet needle 141 to its piercing orientation.

Figure 13:
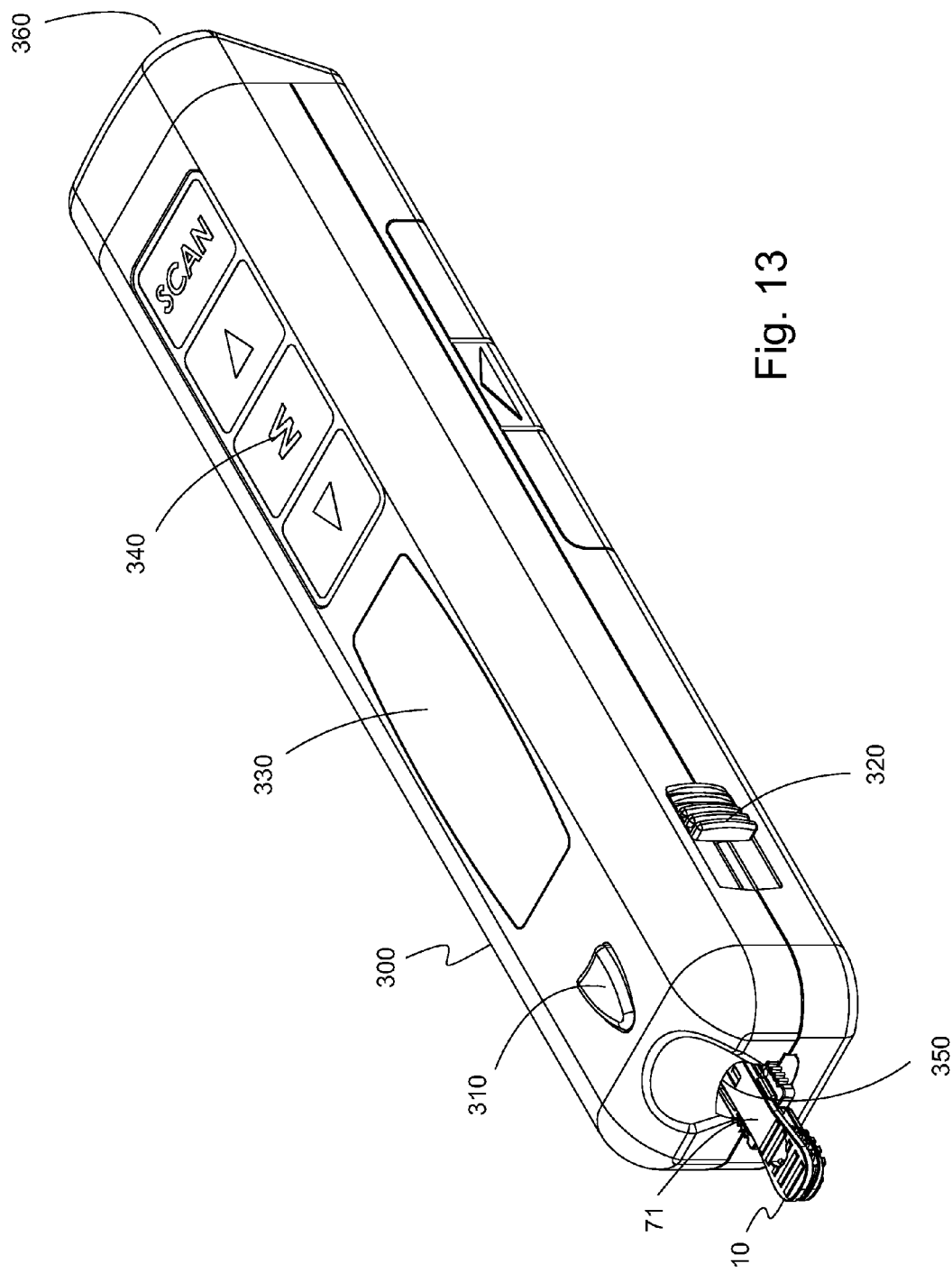
FIG. 13 is a front perspective view of the single-use lancet cartridge and meter showing the lancet cartridge mounted into a meter housing.
Figure 14:
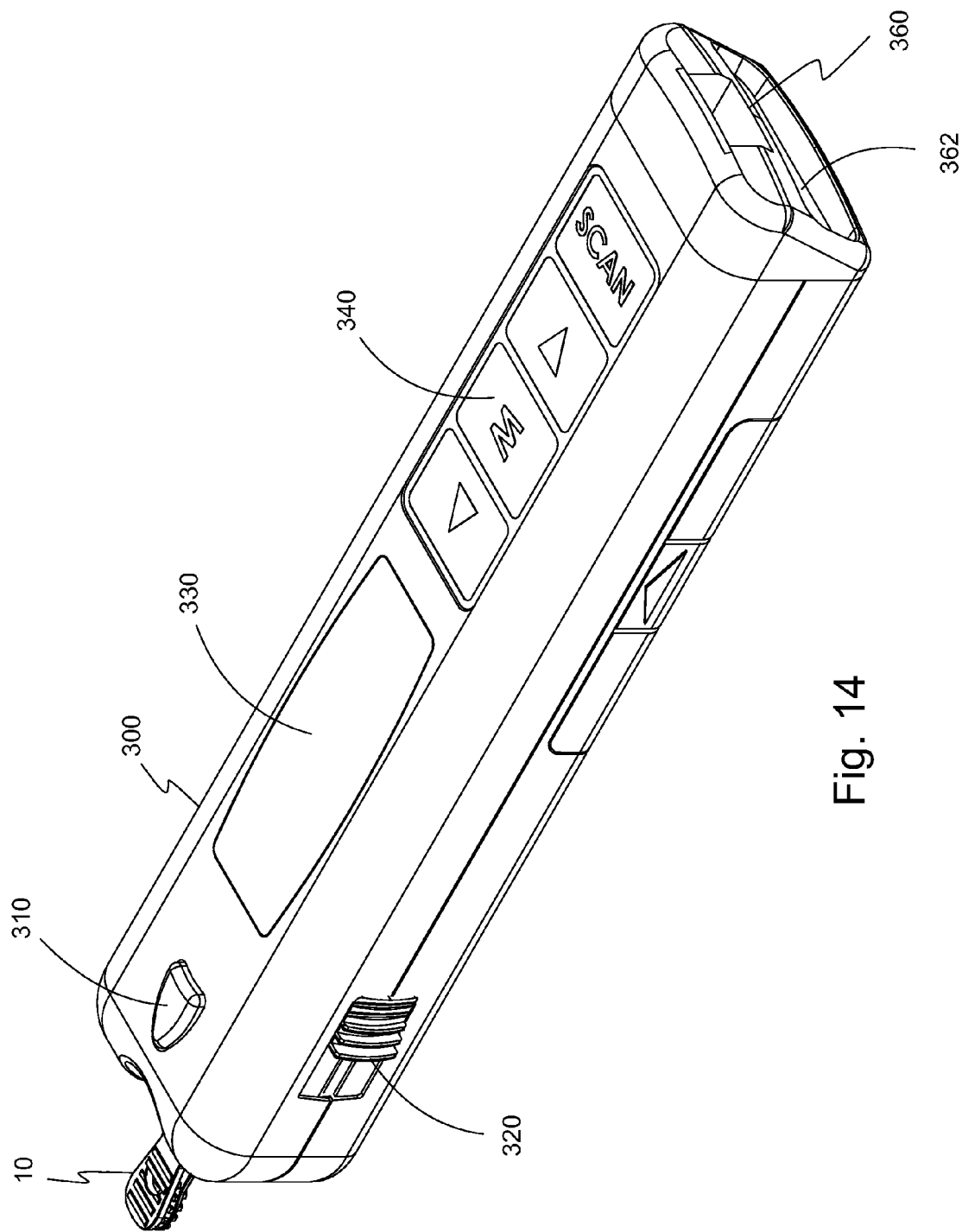
FIG. 14 is a rear perspective view of the single-use lancet cartridge and meter showing the scanner window coupled to the meter housing.

FIG. 13 is a front, perspective view of a portable meter housing 300 and lancet cartridge 10. Meter housing 300 includes display 330, an activating trigger 310, a cartridge ejector 320, a control panel 340, a cartridge port 350, and a scanner 360. Lancet cartridge 10, as shown, includes the re-use prevention component 70 that is the piston cocking tab 71. Because piston cocking tab 71 is included, meter housing 300 does not include an arming mechanism for arming the lancet driver piston 80 contained within meter housing 300 since the piston cocking tab 71 arms lancet driver piston 80 when lancet cartridge 10 is inserted into cartridge port 350. FIG. 14 shows a rear, perspective view of the meter housing 300 illustrated in FIG. 13. Scanner 360 includes a scanner window 362 for scanning a bar code that may contain patient information. Meter housing 300 includes an electronic measuring module containing at least a processor and memory for data storage, a scanner module, and a power module. Meter housing 300 may optionally include a charging module, a data transmission module, a data port, etc.

Figure 15:
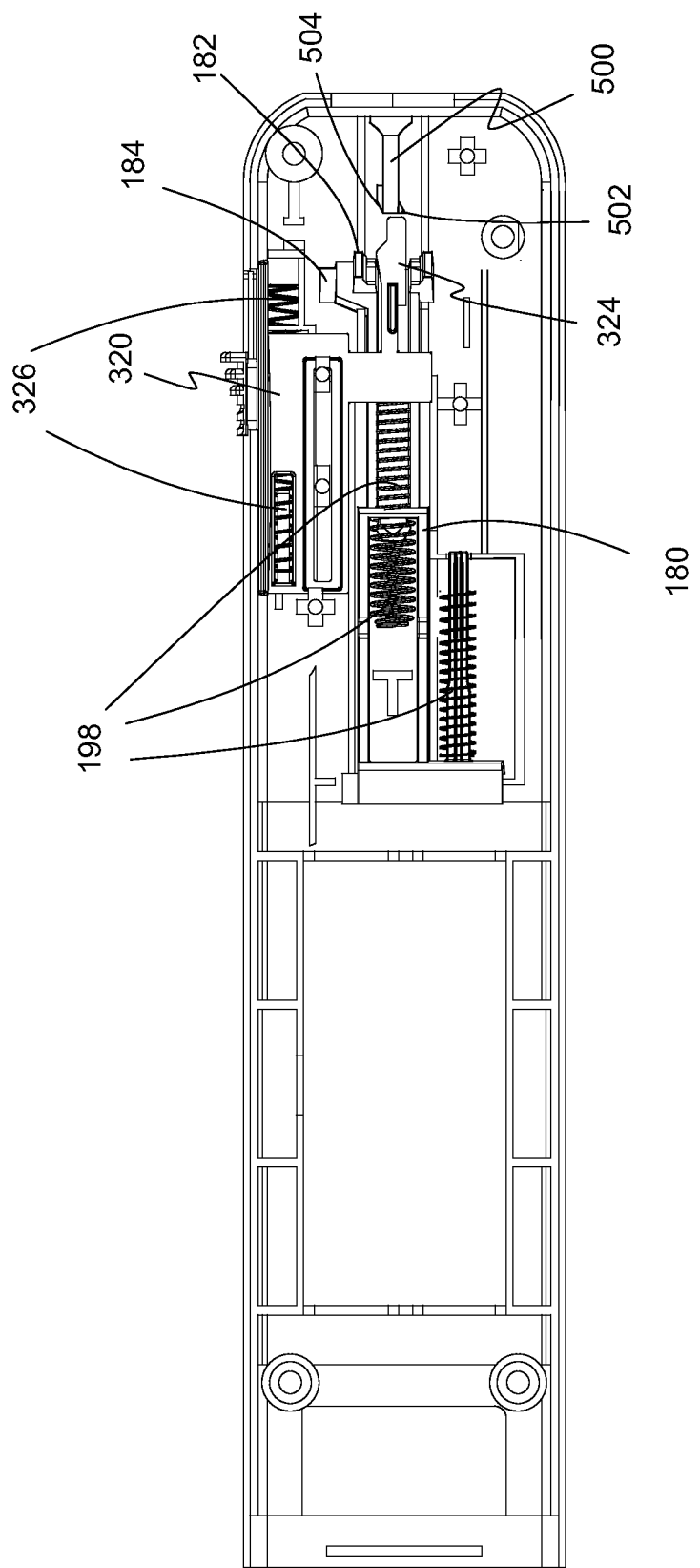
FIG. 15 is a top view of another embodiment of a meter for use with the cocking tab safety lancet.

FIG. 15 illustrates a top view of the inside of meter housing 300 showing only the lancet driver piston 180 and the cartridge ejector 320 for clarity. Lancet driver piston 180 includes a plurality of biasing components 198 such as springs to provide the means for driving the lancet driver piston 180 from the armed position to the piercing orientation and back to the retracted/resting orientation. Cartridge ejector 320 includes a cartridge release arm 324 that engages a cartridge lock member 500 having a cartridge lock 502 that is positioned within the cartridge slot 36 previously shown in FIG. 4 when lancet cartridge 10 is inserted into meter housing 300, and a member release surface 504 that is also engaged by cartridge release arm 324. Cartridge lock member 500 is an elongated, resilient member with enough flexibility to be moved laterally by cartridge release arm 324 but stiff enough to lock and hold lancet cartridge 10 or 100, as the case may be. Cartridge release arm 324 serves two purposes. It engages and moves the cartridge lock out of the cartridge slot 36 while nearly simultaneously ejecting the lancet cartridge 10 out of meter housing 300. Cartridge ejector 320 also includes a plurality of biasing components 326. Noticeably missing from this embodiment of meter housing 300 is a lancet driver piston arming component and a piercing depth gauge.

Figure 16:
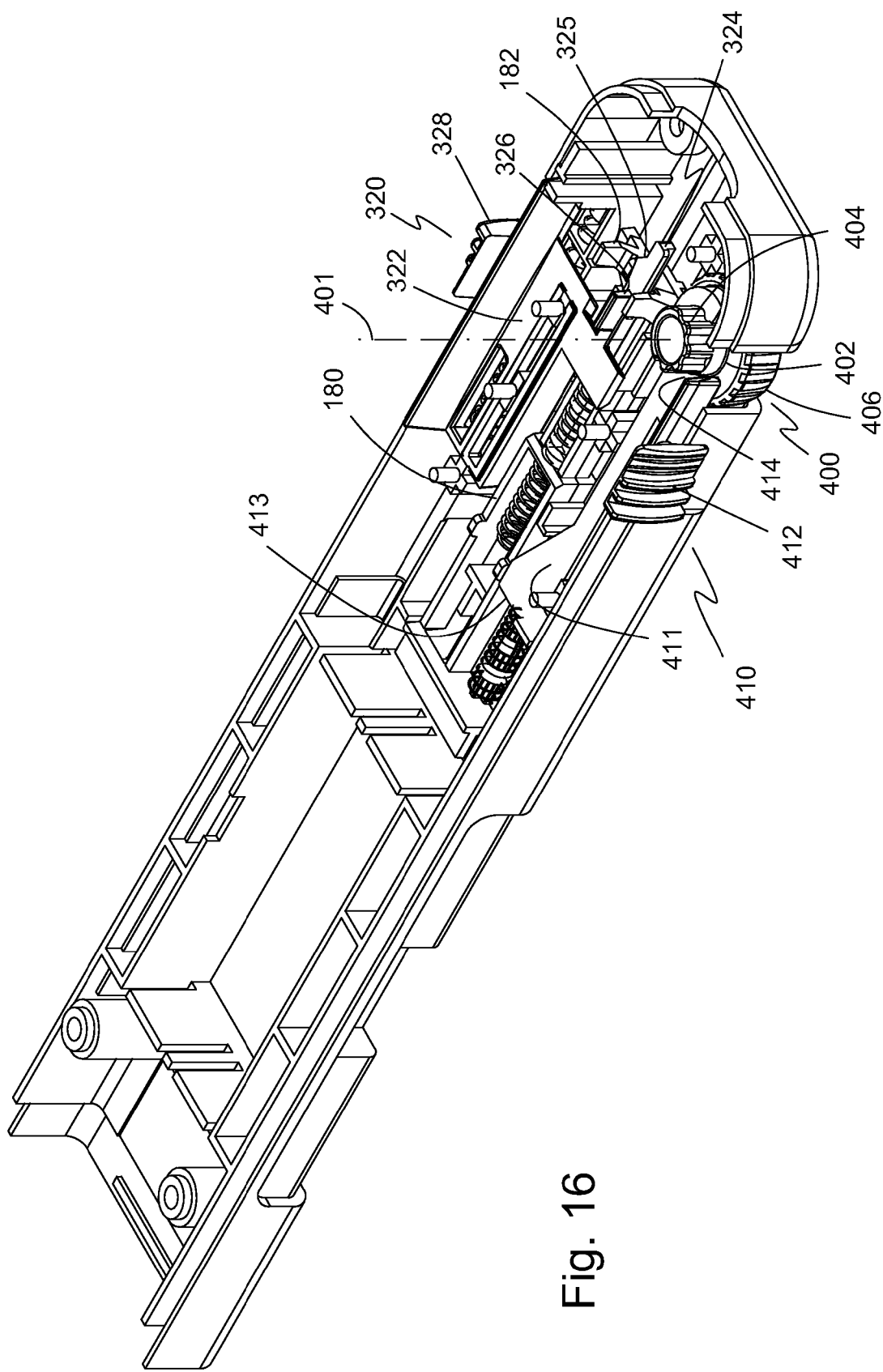
FIG. 16 is a perspective view of one embodiment of a meter for use with the rotating wing safety lancet.
Figure 16A:
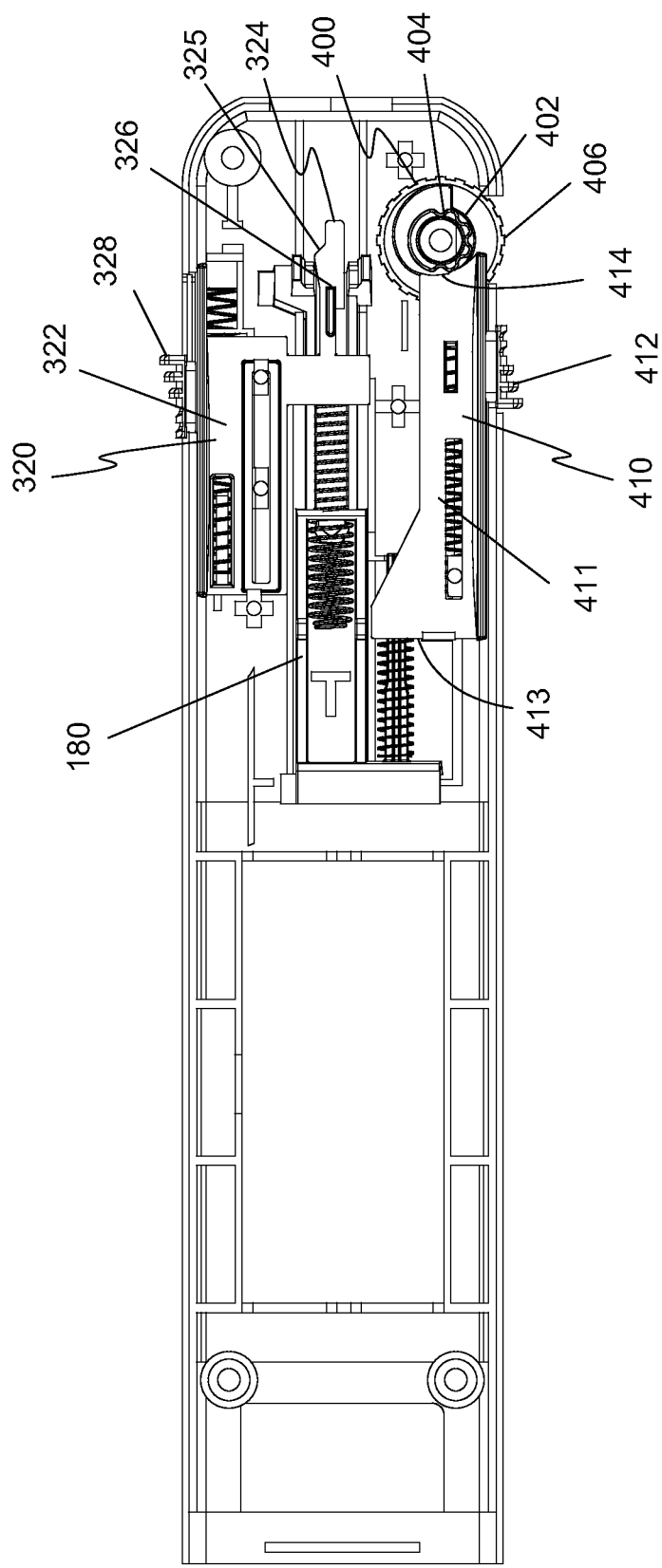
FIG. 16A is a top view of FIG. 16.

Turning not to FIG. 16, there is illustrated an open, perspective view of meter housing 300 for use with lancet cartridge 100. In this embodiment, meter housing 300 includes the multi-use lancet driver piston 180, the cartridge ejector 320, a piercing depth control 400, and a lancet piston arming component 410. Cartridge ejector 320 includes an ejector body 322 with cartridge release arm 324 having a tab engaging surface 325 and a lancet cartridge ejector surface 326, and an ejector button 328 integrally connected to ejector body 322. Lancet piston arming component 410 has an arming member body 411 with a cocking button 412 that is laterally and integrally connected to arming member body 411. When cocking button 412 is activated by the user, arming component 410 slidably engages an arming component end 413 with a portion of driver piston end 185 of the lancet driver piston 180, which moves lancet driver piston 180 into an armed position. Arming component end 413 also acts as a driver piston stop that arrests the forward movement of lancet driver piston 180 toward the piercing orientation, which in turn controls the forward movement of the lancet needle 141 to the piercing orientation. Arming component 410 also includes a piercing depth end 414 that cooperates with piercing depth control 400. Piercing depth control 400 is configured to variably adjust the piercing depth of the lancet needle 141 into the specimen and is manually controlled by a user. Piercing depth control 400 is an adjusting wheel that includes an arcuate surface 402 having a variable radius relative to a wheel axis 401 that engages the piercing depth end 414 of arming component 410. Piercing depth control 400 also includes a detent engaging structure 404 that cooperates with a fixed detent (not shown) of the meter housing 300. Detent engaging structure 404 has indentations for receiving the detent. The indentations represent pre-determined settings for the piercing depth of the lancet needle 141 and coincide with specific locations of the arcuate surface 402. An outer surface portion 406 of piercing depth control 400 extends outside of the meter housing 300 for manipulation by the user. FIG. 16A is a top view of FIG. 16 to more clearly show the various components of piercing depth control 400, arming component 410, and cartridge ejector 320.

To use the lancet cartridge 10 having a piston cocking tab 71, lancet cartridge 10 is inserted into a meter housing 300 configured for use with lancet cartridge 10. The process of inserting lancet cartridge 10 into meter housing 300 causes piston engageable surface 72 of the piston cocking tab 71 to engage and push the lancet driver piston within the meter housing 300 into an armed position. After removing the needle safety cap 50, which simultaneously removes piston cocking tab 71 from lancet cartridge 10, lancet cartridge 10 is ready for its single use. Because the piston cocking tab 71 is simultaneously removed from the lancet cartridge 10 when the needle safety cap 50 is removed, the mechanism to arm the lancet driver piston is also removed. Thus, subsequent use of the lancet cartridge to pierce another or the same specimen is defeated.

To use the lancet cartridge 100 having a rotatable drive wing 171, lancet cartridge 100 is inserted into a meter housing 300 configured for use with lancet cartridge 100. Either before or after lancet cartridge 100 is inserted into meter housing 300, lancet driver piston 180 is armed by the user cocking the lancet driver piston using the lancet piston arming component 410. Lancet piston arming component 410 is slidably moved rearwardly pushing lancet driver piston 180 into an armed position until the trigger release stop 184 is engaged by trigger release 310. After removing the needle safety cap 150, lancet cartridge 100 is ready for its single use. Upon activating the armed lancet driver piston 180 by pressing the trigger 310, lancet driver piston 180 moves towards the first drive wing portion 174 of the rotatable drive wing 172. During this movement, the pawl deflector surface 194 of pawl 190 contacts first drive wing portion 174 and because a drive wing stop 144 on lancet body 142 prevents the rotatable drive wing 170 from rotating due to the impact of the pawl deflector surface 194 with first drive wing portion 174, pawl 190 is deflected below first drive wing portion 174 and automatically returns to its non-deflected position just before drive wing piston surface 182 engages first drive wing portion 174. The lancet driver piston 180 then impacts first drive wing portion 174 and continues to the piercing orientation. Subsequent to reaching the piercing orientation, wing rotating surface 196 of pawl 190 engages first wing portion 174 and rotates rotatable drive wing 172 to position first drive wing portion 174 within lancet housing 120 so that first drive wing portion 174 no longer extends out of lancet housing 120 and no longer presents a surface upon which drive wing piston surface 182 can engage. The rotation of drive wing 172 into the lancet housing 120 effectively removes the presentation of a contact surface to the lancet driver piston 180 and prevents re-use of the lancet 140 regardless of any re-arming and re-activating of lancet driver piston 180 by the user.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A single-use lancet cartridge for inserting into a multi-use lancet driver assembly, the single-use lancet cartridge comprising:
   an elongated lancet housing with an open end;
   a lancet within the lancet housing and movable between a retracted and resting orientation to a piercing orientation through the open end; and
   a re-use prevention component incorporated within the lancet cartridge and oriented to cooperatively engage with a driver piston of the multi-use lancet driver assembly external to the lancet cartridge only one time thereby preventing the lancet from being moved into a piercing orientation a second time, the re-use prevention component being a rotatable drive wing having at least a first drive wing portion directly connected to a lancet body of the lancet and rotatable between a first position and a second position wherein the first position has the first drive wing portion extending laterally from a side of the lancet and wherein the second position has the first drive wing portion failing to extend beyond the side of the lancet, wherein when the first drive wing portion is in the first position the first drive wing portion is presented for cooperative engagement with the driver piston and when in the second position the first drive wing portion is incapable of cooperative engagement with the driver piston.

2. The single-use lancet cartridge of claim 1 wherein the rotatable drive wing has a second drive wing portion directly connected to the lancet body of the lancet opposite the first drive wing portion and rotatable between a first position and a second position wherein the first position has the second drive wing portion extending laterally from an opposite side of the lancet and wherein the second position has the second drive wing portion failing to extend beyond the side of the lancet wherein when the second drive wing portion is in the first position the second drive wing portion is presented for cooperative engagement with the driver piston and when in the second position the second drive wing portion is incapable of cooperative engagement with the driver piston.

3. The single use lancet cartridge of claim 2 further comprising an anti-rotation wing stop cooperatively engageable with the second drive wing portion.

4. The single-use lancet cartridge of claim 1 further comprising a test strip integrally connected to the elongated lancet housing.

5. A lancet system with safety feature, the system comprising:
   a multi-use lancet driver assembly having a driver piston, the multi-use lancet driver assembly contained within a meter housing; and
   a single-use lancet cartridge having a lancet housing with an open end, a lancet within the lancet housing and movable between a retracted and resting orientation to a piercing orientation through the open end, and a re-use prevention component incorporated within the lancet cartridge and oriented to cooperatively engage with the driver piston of the multi-use lancet driver assembly only one time thereby preventing the lancet from being moved into a piercing orientation a second time, the re-use prevention component being a rotatable drive wing having at least a first drive wing portion directly connected to a lancet body of the lancet and rotatable between a first position and a second position wherein the first position has the first drive wing portion extending laterally from a side of the lancet and wherein the second position has the first drive wing portion failing to extend beyond the side of the lancet, wherein when the first drive wing portion is in the first position the first drive wing portion is presented for cooperative engagement with the driver piston and when in the second position the first drive wing portion is incapable of cooperative engagement with the driver piston.

6. The lancet system of claim 5 wherein the rotatable drive wing has a second drive wing portion directly connected to the lancet body of the lancet opposite the first drive sing portion and rotatable between a first position wherein the second drive wing portion extends laterally from an opposite side of the lancet and a second position wherein the second drive wing portion fails to extend beyond the side of the lancet wherein when the second drive wing portion is in the first position the second drive wing portion is presented for cooperative engagement with the driver piston and when in the second position the second drive wing portion is incapable of cooperative engagement with the driver piston.

7. The lancet system of claim 6 further comprising an anti-rotation wing stop cooperatively engageable with the first drive wing portion, the second drive wing portion or both.

8. The lancet system of claim 6 wherein the drive piston includes a deflectable drive wing pawl extending beyond the end of the drive piston, the deflectable drive wing pawl having a wing rotating surface engageable with the rotatable drive wing after the lancet is moved into a piercing orientation by the drive piston thereby causing the rotatable wing to rotate into the first elongated side opening.

9. The lancet system of claim 5 further comprising a lancet cartridge lock within the meter housing, the lancet cartridge lock having an elongated and biasing member with a locking tab extending laterally from the biasing member and situated for cooperative and biasing engagement with a notch in the bottom of the lancet housing when a lancet cartridge is inserted into a lancet cartridge receiving port of the meter housing.

10. The lancet system of claim 5 further comprising a cartridge ejector having an ejector body with a cartridge engaging member having a tab engaging surface and a lancet cartridge ejector surface situated within the meter housing, and an ejector button laterally and integrally connected to the ejector body and disposed outside of the meter housing for slidably ejecting the lancet cartridge wherein the tab engaging surface is positioned to engage the locking tab before the lancet cartridge ejector surface engages the lancet cartridge when the ejector button is slidably engaged.

11. The lancet system of claim 5 further comprising a piercing depth control having an arcuate surface with a variable radius relative to the piercing depth control axis that engages a piercing depth end of the arming member body situated within the meter housing and an outer surface a portion of which extends outside of the meter housing for setting the position of the arcuate surface relative to the piercing depth end of the arming member body.

12. The lancet system of claim 5 wherein the lancet driver assembly further includes an actuator button cooperatively connected to the driver piston when the driver piston is in a cocked orientation.

* * * * *